United States Patent [19]
Brody

[11] Patent Number: 5,564,222
[45] Date of Patent: Oct. 15, 1996

[54] METHOD AND ARTICLES FOR KILLING TERMITES

[75] Inventor: Yaakov Brody, Pikesville, Md.

[73] Assignee: Environmental Laboratories, Inc., Baltimore, Md.

[21] Appl. No.: 329,907

[22] Filed: Oct. 27, 1994

Related U.S. Application Data

[63] Continuation-in-part of Ser. No. 160,733, Dec. 3, 1993, abandoned.

[51] Int. Cl.$^6$ ..................................................... A01M 1/02
[52] U.S. Cl. ........................................... 43/124; 43/132.1
[58] Field of Search ........................... 43/124, 107, 111, 43/114, 132.1; 424/413, 414, 415, 416, 660, 659, 658, 657

[56] References Cited

U.S. PATENT DOCUMENTS

| | | | |
|---|---|---|---|
| 612,839 | 10/1898 | Gallinowsky | 424/413 |
| 2,795,527 | 6/1957 | Gopp | 167/48 |
| 2,883,322 | 4/1959 | Whipple | 167/39 |
| 3,070,495 | 12/1962 | Esenther et al. | 167/48 |
| 3,858,346 | 1/1975 | Bailey | 43/124 |
| 3,940,875 | 3/1976 | Basile | 43/124 |
| 4,363,798 | 12/1982 | D'Orazio | 424/84 |
| 4,388,352 | 6/1983 | Allen et al. | 427/391 |
| 4,504,468 | 3/1985 | Brill et al. | 424/147 |
| 4,661,157 | 4/1987 | Beauford et al. | 106/18.13 |
| 4,861,669 | 6/1989 | Demarest et al. | 43/131 |
| 5,089,483 | 2/1992 | Tsuda et al. | 424/660 |
| 5,194,323 | 3/1993 | Savoy | 428/305.5 |
| 5,224,315 | 7/1993 | Winter, IV | 53/309.8 |
| 5,304,237 | 4/1994 | Barth et al. | 106/18.3 |

FOREIGN PATENT DOCUMENTS

| | | |
|---|---|---|
| 3610374 | 10/1987 | Germany. |
| 2114003 | 8/1983 | United Kingdom. |

OTHER PUBLICATIONS

U. S. Borax Inc., Material Safety Data Sheets for TIM–BOR Insecticide, 1993.
Noirot, "Borates And Termite Control", Alternate Termite Control, PCOC, Sep. 1992, pp. 1–4.
Suomi et al, "Control Of The Structure–Infesting Beetle, *Hemicoelus gibbicollis* (Coleoptera:Anobiidae) With Borates", Journal of Economic Entomology, Aug. 1992, pp. 1188–1193.

*Primary Examiner*—Chuck Y. Mah
*Attorney, Agent, or Firm*—Leydig, Voit & Mayer

[57] ABSTRACT

An article for poisoning of termites without poisoning the soil is a cellulose body impregnated with a borate salt. The cellulose body may be wood, paper, or laminated paper that is placed on or in soil. These articles are placed in contact with the soil at spaced apart intervals having a regular interval near a structure to be protected from termite attack, near a termite infestation, or near a termite-attracting feature. The articles are impregnated preferably with a sodium borate salt, such as disodium octaborate tetrahydrate or disodium tetraborate decahydrate.

11 Claims, 2 Drawing Sheets

METHOD AND ARTICLES FOR KILLING TERMITES

This disclosure is a continuation-in-part of U.S. patent application Ser. No. 08/160,733, filed Dec. 3, 1993 now abandoned.

FIELD OF THE INVENTION

The present invention relates to a method of poisoning termites without poisoning the soil and articles useful in the method of poisoning termites.

BACKGROUND OF THE INVENTION

Termites are well known throughout most areas of the world. These insects that attack and destroy wooden structures are classified into four principal categories, i.e., subterranean, formosan, damp wood, and dry wood. The invention is particularly directed to poisoning of subterranean, damp wood, and formosan termites. (Dry wood termites live in wood with relatively small moisture content in particular areas of the world and are not present in the soil.) Many methods for killing termites have been practiced over the years. Frequently, some termite-killing chemical is applied to the soil in the vicinity of a structure that is to be protected from termites. Many of the termiticides that have been used have lasted in the soil for a long time and do not break down into innocuous residues. An example of such a long-lasting chemical that has been used for many years is chlordane. However, chlordane and other halogenated insecticides, such as DDT, aldrin, dieldrin, and heptachlor have harmful effects. The residues of these chlorinated insecticides remain in the soil for very long periods of time and it is known or believed that some of these insecticides are dangerous to humans and higher life forms including other mammals. Because of these environmental hazards, use of many of these insecticides has been severely limited or prohibited. Typically, these insecticides are applied directly to the soil near a structure to be protected, forming a subterranean "curtain" or barrier that kills termites that attempt to pass through the barrier. These insecticides not only are hazardous because of their long lifetime and the nature of the residues they leave but are also hazardous to the persons involved in the manufacture and application of the insecticides to the soil.

As a substitute for introducing a "curtain" of an insecticide into the soil adjacent a structure to be protected against termite infestation, sometimes structures are built of wood that has been pressure-treated to retard termite infestation. Generally, the pressure-treated wood is not impregnated with the treating material through its entire thickness so that termites and rot invade the parts of that pressure-treated wood that has not been impregnated with the protecting material. Many of the materials used for those wood treatments are themselves dangerous, both in application, as are the insecticides, and in use through the risk of leaching or other escape of the toxic materials. For example, the material with which the wood is treated has a finite vapor pressure at normal temperatures so that some of the material can escape slowly over time into a structure. Pressure-treated wood that is commonly sold as lasting for a long period of time, even in direct contact with soil, may contain arsenic, heavy metals, or other toxic elements that can undesirably escape into the ambient or leach into contacting fluids or soil, leaving potentially toxic residues.

SUMMARY OF THE INVENTION since termites cannot be eliminated, it is desirable to provide a simple article and technique that can eradicate termite colonies without poisoning the soil or introducing elements into the soil that present an unreasonable health hazard.

In one aspect of the invention, a structure is protected from termite attack without poisoning soil by placing in or on the soil, at spaced apart intervals, cellulose bodies impregnated with a borate salt or that are impregnated by adding a water soluble borate salt and water to the article. Alternatively, an area subject to termite infestation or already infested is surrounded by the cellulose bodies to prevent invasion by termites or to prevent escape of termites.

According to another aspect of the invention, an article for poisoning termites without poisoning soil comprises a tapered cellulose body impregnated with a borate salt. The article is easily inserted into soil.

Another aspect of invention concerns a kit including a hollow cellulose article having a tapered end for easy insertion into soil and a water soluble borate salt for placing in the hollow article so that when the borate salt is dissolved in water added to the article, the cellulose is impregnated with the salt.

BRIEF DESCRIPTION OF THE DRAWINGS

Like elements are given the same reference numbers in all figures.

DETAILED DESCRIPTION OF PREFERRED EMBODIMENTS

In order to avoid poisoning of the soil in using a method for preventing attack of a structure by termites, a termiticide must be chosen carefully. Preferred termiticides that do not poison the soil are borate salts. Boron is widely present in the environment and is a nutrient for plant life. Boron appears naturally in fruits and vegetables and is consumed by most humans in small amounts every day. In other words, borate salts are good choices for termiticides because of their low mammalian toxicity.

Borate salts are well known as termiticides. For example, $Na_2B_8O_{13} \cdot 4H_2O$ (disodium octaborate tetrahydrate) is presently being sold as a termiticide by U.S. Borax Inc. of Los Angeles, Calif. under the registered trademark TIM-BOR. $Na_2B_4O_7 \cdot 10H_2O$ (disodium tetraborate decahydrate) is also known to be an effective termiticide. These sodium borate salts have acceptable degrees of solubility in water for use in the present invention. It is believed that borate salts are slow acting termiticides that kill a protozoan living within the gut of termites. That protozoan is essential to the digestion of cellulose. Thus, when a termite ingests the borate salt, it does not die instantly but gradually starves as the protozoa die and the termite no longer is nourished by ingested cellulose.

In their social organization, a certain class of termites forage for food to feed other classes of termites in the society. When the foraging termites return to a colony and feed the ingested, slow-acting borate salt to nymphs, soldiers, and the termite queen, those other termites are also poisoned. The termiticide may also be spread when poisoned termites die and are cannibalized. Gradually, an entire colony can be decimated by feeding on a borate salt, directly or indirectly.

Since borate salts are well recognized as effective, slow-acting termiticides, some means must be provided for supplying the termiticide to foraging termites. The foraging termites seek cellulose as food, for example, by burrowing through soil or debris or materials covering soil, such as dead or decaying vegetation, including mulch. In the invention, cellulose articles impregnated with a borate salt are placed in or on the soil near a structure to be protected from termite attack, near a termite infestation, or near a feature, such as a tree stump, likely to attract termites. The foraging termites eat the cellulose of the articles, thereby ingesting the termiticide and carrying it back to the termite colony.

Figure 1:
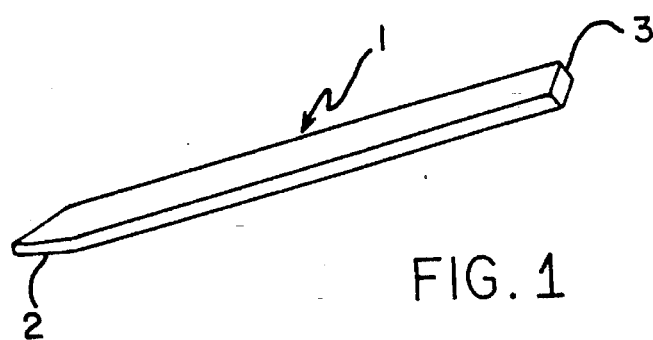
FIG. 1 is a perspective view of a cellulose body impregnated with a borate salt according to an embodiment of the invention.
Figure 2A:
FIGS. 2(a) and 2(b) are cross-sectional views of examples of embodiments of articles according to the invention.

An example of such an article for supplying the borate salt to termites, a wooden stake 1, is shown in FIG. 1. The stake 1 includes a tapered end 2 for easy insertion into soil, for example, by pushing a driving end 3 or driving the end 3 with a hammer. The stake can have any cross-sectional shape, such as rectangular, as shown in FIG. 1, or circular, as shown in the end view of FIG. 2(a). The tapered end may be pointed, as shown in FIG. 1, or may have a more rounded tapered end. The stake is impregnated with a borate salt so that when a termite burrowing through the soil reaches the stake and ingests the cellulose, i.e., wood, of the stake, it ingests the termiticide.

Any appropriate borate salt can be employed to impregnate the stake 1, such as disodium octaborate tetrahydrate or disodium tetraborate decahydrate. An aqueous solution of the salt is prepared and a cellulose article, such as the stake 1, is immersed in the solution for a sufficient amount of time for the solution to be absorbed by the stake or other cellulose article. Soaking of cellulose articles in a borate salt solution of at least 0.5 weight percent concentration and up to 20 weight percent concentration is preferred. The percentage of the borate salt in the cellulose article may vary. If the concentration is too high, termites may be repelled and not eat the cellulose. If the concentration is too low, loss of the borate salt into the adjacent soil from the cellulose article may exhaust the effective supply of the salt prematurely. In order to improve the wetting of cellulose and absorption of the solution by the cellulose, a surfactant may be added to the aqueous solution. Among the surfactants that assist in wetting cellulose articles are soaps, detergents, floatation agents, and ethylene glycol. All of these surfactants lower the surface tension of the water in the solution. In order to increase the speed with which the salt is taken up by a cellulose article, a pressure exceeding one atmosphere may be applied to the surface of the solution containing cellulose articles being impregnated with the borate salt.

Figure 2B:
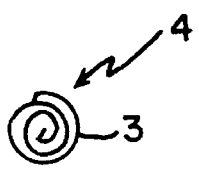
Figure 3A:
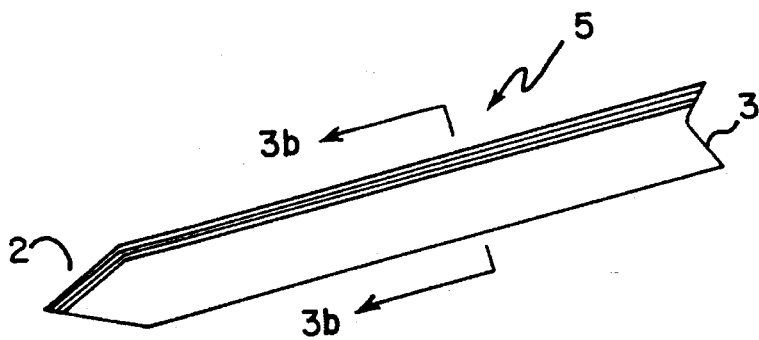
FIGS. 3(a) and 3(b) are a perspective and sectional view, respectively, of another embodiment of an article according to the invention.
Figure 3B:
Figure 4A:
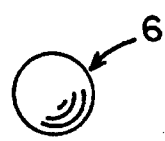
FIGS. 4(a), 4(b), and 4(c) are perspective views of alternative embodiments of articles according to the invention.
Figure 4B:
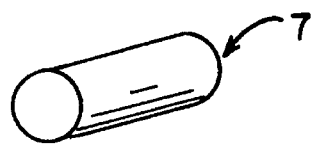

The article impregnated with the borate salt may be any cellulose body and is not limited to wood. For example, an article 4 similar to the stake 1 can be made by rolling a heavy paper, including cardboard, in a spiral form, as shown in a view of the driving end 3 in FIG. 2(b). The spiral is held together with an appropriate adhesive. Still another appropriate article for impregnation with the borate salt can be made from laminations of heavy paper, including cardboard formed generally in an L cross-sectional shape for strength and having a tapered end. The laminated structure can be pushed into or hammered and driven into the soil. The laminations are held together with an adhesive. Such an article 5 having a tapered end 2, in this case a pointed end, and a driving end 3 is shown in a perspective view in FIG. 3(a) and in a cross-sectional view in FIG. 3(b). As with the wooden stakes, paper or cardboard articles are conveniently impregnated with a borate salt by soaking in an aqueous solution of the salt. Still other cellulose articles in the form of spheres 6 and pellets 7, as illustrated in FIGS. 4(a) and 4(b), respectively, or other treated cellulose bodies 7 with a relatively rough surface, such as the article illustrated in FIG. 4(c), may be impregnated with a borate salt. The spheres, pellets, or irregular articles can be easily made from wood, paper fibers, or laminated paper, including cardboard, that is cut, compressed, extruded or otherwise processed into the desired shape. Although not preferred because of its large content of non-cellulose material and its low absorbance, the articles might also be made of composite materials, such as particle board or chip board.

A particularly desirable form of the invention is a borate salt impregnated mulch. As used here, mulch means any conventional cellulose mulch product, such as wood chips, tree bark, and other commonly sold wood articles and by-products, that are used as a ground cover for decorative or weed control purposes. The mulch is treated with a borate salt, for example, by spraying with an aqueous solution of the salt, to produce a product according to the invention.

Figure 5A:
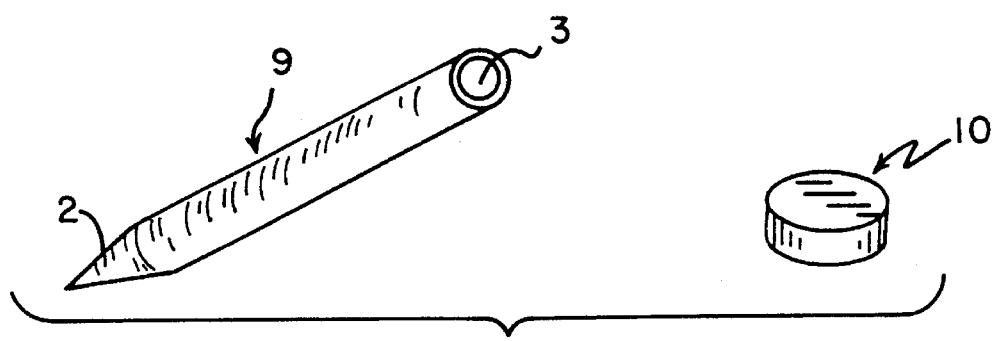
FIGS. 5(a), 5(b), and 5(c) are views of articles comprising embodiments of kits according to the invention.
Figure 5B:
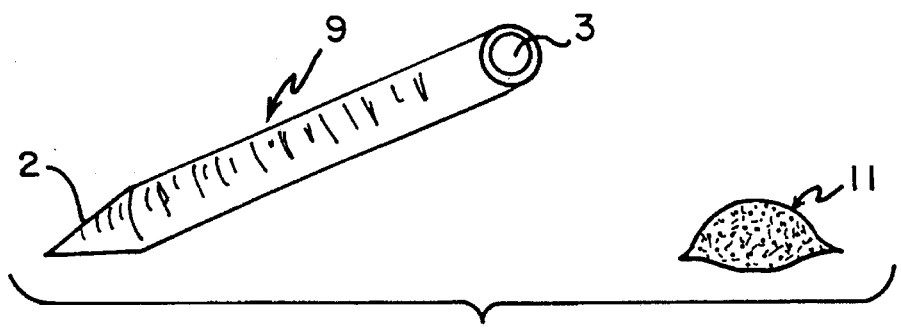
Figure 5C:
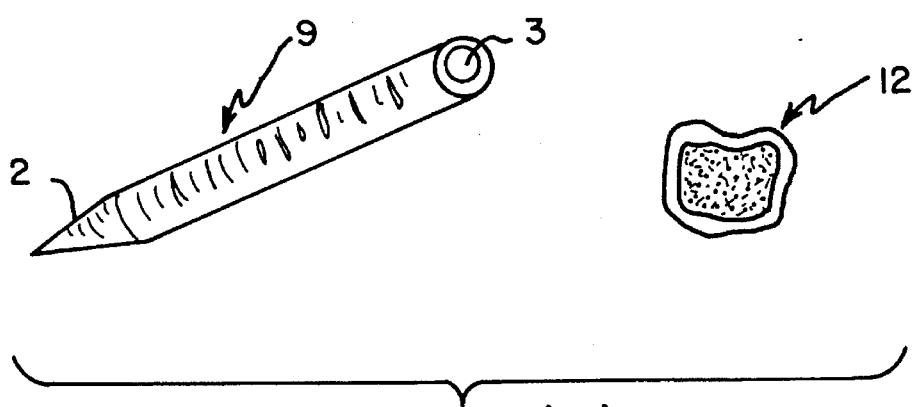

The cellulose articles may be impregnated with the borate salt at the time of their installation in the soil rather than during manufacture at a site remote from the place of installation. In that instance, kits of the articles and the borate salt are supplied together for use by the person installing the cellulose articles. Examples of kits are illustrated in FIGS. 5(a), 5(b), and 5(c). In each instance, a hollow, i.e., partially tubular, cellulose article 9 includes a tapered end 2 and a driving end 3. A preferred hollow body is made by spirally wrapping paper or cardboard. The hollow article 9 is pushed or driven into the soil and, thereafter, the other part of the kit is employed to impregnate the article with the borate salt. In the kit illustrated in FIG. 5(a), a borate salt is provided in the form of a capsule or tablet 10 and is inserted in the driving end 3 of the article 9. Thereafter, the article 9 is filled with water so that the capsule or tablet 10 dissolves. The figure is not drawn to scale and the capsule or tablet 10 has a size that allows its easy insertion into the open part of the driving end 3 of the cellulose article 9. The tablet includes a sufficient quantity of the borate salt so that when water enters the article 9, the tablet or capsule dissolves and forms a solution impregnating the cellulose article 3 with the borate salt. The solution has a concentration of at least one-half percent of the salt.

Another kit embodiment is shown in FIG. 5(b) in which the borate salt is supplied in the form of a powder 11 that is poured into the open end of the cellulose article 9. In the kit embodiment illustrated in FIG. 5(c), the borate salt powder in a predetermined appropriate quantity for the size of the cellulose article 9 is supplied as a packet 12 including a water soluble or water permeable film that dissolves or allows the borate salt to pass when the cellulose article 9 containing the packet 12 is filled with water. Similar packets containing measured quantities of the borate salt instead of the borate salt powder 11, may be furnished to simplify the addition of the proper quantity of the salt to the cellulose article 9. The packets are supplied inside the cellulose article. In other alternatives, the kit may include a removable plastic tube internal or external to the cellulose body. The tube protects the borate salt from moisture until the cellulose body is placed in contact with the soil after which the plastic tube is removed.

Although the cellulose article 9 shown in each of FIGS. 5(a)–5(c) has an open driving end 3, the cellulose article 9 may also be supplied with a closed end for simplified driving of the tapered end of the soil. The driving end may be removable. The dry borate salt in powder or compressed form may already be present inside a hollow article with pointed and closed ends. A hole may be opened at the end of the article for the introduction of water, the article may be submerged in water before installation in the soil, or the article may be repeatedly saturated with water after installation so that water enters the article and dissolves the borate salt contained within the article.

The articles impregnated with a borate salt before or after installation can be placed in the soil in various ways in order to form a subterranean "fence" along part of or around all of a structure, a termite infestation, or a feature, such as a tree stump, likely to attract termites. In that arrangement, if termites are present, the termites preferentially consume the cellulose article containing the borate salt and carry the borate salt or its byproducts to other termites in their colony so that all termites in the colony are ultimately killed. In this application, the borate salt is not a bait that attracts termites and kills them immediately. The cellulose attracts the termites. The termites carry the borate salt back to the colony where the lethal poisoning occurs.

The preferred method of installing the tapered cellulose articles is to insert them into soil, approximately vertically. Preferably, the cellulose articles are placed six to twelve inches from a structure to be protected, from a termite colony, or from a termite-attracting feature and are spaced apart at regular intervals from neighboring articles. For example, a spacing of about three feet between adjacent articles is preferred. Additional protection can be provided by installing a second "fence" outside the first "fence", for example, about three feet away from the first array of articles. In the outer array, the articles are spaced from each other by about the same distance as in the inner array of articles. The articles can be quickly and efficiently installed to contain and rid an area of termites as well as to protect an adjacent structure or termite attracting feature from termite infestation.

Figure 4C:

When the cellulose articles are spheres or pellets or particles, as illustrated in FIGS. 4(a), 4(b), and 4(c), or mulch, i.e., impregnated wood chips and/or bark, they may be installed in various ways. For example, instead of inserting tapered articles into the soil, a tool, such as a pointed rod, may be used to open a channel into the soil, temporarily, into which the spheres or particles are dropped. The spheres, pellets, or treated mulch can also be distributed on the surface of the soil. The distribution of spheres or pellets may simulate the rows of articles as described above. In addition, the pellets or spheres can be mixed with or placed under untreated mulch or other ground cover that might harbor termites adjacent to or near a structure to be protected, adjacent a termite infestation, or adjacent a termite-attracting feature. Treated mulch is applied, just as untreated mulch, as a decorative or weed control ground cover. Termites that reach the space between the mulch and the soil eat the treated mulch and carry the borate salt back to the colony to kill large numbers of termites.

An existing row of borate salt impregnated articles or mulch can be replaced or supplemented from time-to-time depending upon the rate of deterioration, the degree of termite attack of the cellulose articles as determined by inspecting the articles or mulch, or the loss of the borate salt. The borate salt may leach from the impregnated articles and/or dissolve in moisture and spread through the soil. The result is a "certain" of termiticide that can be ingested by termites even if the cellulose articles are not directly attacked. Because of the very low or non-existent mammalian toxicity of the borate salt, spreading of termite colonies, attack of a structure by termites, and attraction of termites is prevented by the invention without poisoning the soil by introducing a toxic material or leaving undesirable residues. In addition, the cellulose articles can be prepared and used without health risks to the workers manufacturing or installing them.

The invention has been described with respect to certain specific embodiments. However, additions and modifications within the spirit of the invention will occur to those of skill in the art from the foregoing description. Accordingly, the scope of the invention is limited solely by the following claims.

I claim:

1. A method of eradicating termites without poisoning soil comprising driving into the soil, at spaced apart intervals, cellulose stakes impregnated with a borate salt.

2. An article for poisoning termites without poisoning soil comprising a cellulose stake having a tapered end and impregnated with a borate salt.

3. The article of claim 2 wherein the cellulose stake is wood.

4. The article of claim 2 wherein the cellulose stab is paper.

5. The article of claim 2 wherein the cellulose stake is laminated paper.

6. The article of claim 2 wherein the cellulose stake, is hollow.

7. The article of claim 2 wherein the borate salt is a sodium borate salt.

8. A kit for making an article for poisoning termites without poisoning soil comprising a hollow cellulose stake and a quantity of a water soluble borate salt, the borate salt being placed within the hollow cellulose stake and dissolving when water is supplied to the hollow cellulose stake, thereby impregnating the cellulose stake with the borate salt.

9. The kit of claim 8 wherein the cellulose stake has a tapered end.

10. The kit of claim 9 wherein the hollow cellulose stake has an open end opposite the tapered end.

11. The kit of claim 8 wherein the borate salt is a sodium borate salt.

\* \* \* \* \*

UNITED STATES PATENT AND TRADEMARK OFFICE
CERTIFICATE OF CORRECTION

PATENT NO. : 5,564,222
DATED : October 15, 1996
INVENTOR(S) : Brody

It is certified that error appears in the above-indentified patent and that said Letters Patent is hereby corrected as shown below:

Column 6, Line 40, change "stab" to --stake--.

Signed and Sealed this

Twenty-fourth Day of December, 1996

Attest:

BRUCE LEHMAN

*Attesting Officer*     *Commissioner of Patents and Trademarks*